United States Patent [19]

Davies et al.

[11] 4,177,253
[45] Dec. 4, 1979

[54] MAGNETIC PARTICLES FOR IMMUNOASSAY

[75] Inventors: George E. Davies, Macclesfield, England; Jiri Janata, Salt Lake City, Utah

[73] Assignee: Imperial Chemical Industries Limited, United Kingdom

[21] Appl. No.: 813,422

[22] Filed: Jul. 6, 1977

[30] Foreign Application Priority Data

Jul. 30, 1976 [GB] United Kingdom ............... 31839/76

[51] Int. Cl.² ............................................. G01N 33/00
[52] U.S. Cl. .......................................... 424/1; 424/12; 252/62.52; 427/212; 23/230 B
[58] Field of Search ..................... 424/1, 12; 23/230 B; 252/62.52, 62.54, 62.55, 62.59; 209/213; 427/212

[56] References Cited

U.S. PATENT DOCUMENTS

| | | | |
|---|---|---|---|
| 2,939,804 | 6/1960 | Schossberger et al. | 427/212 |
| 3,175,935 | 3/1965 | Vanstrum | 252/62.52 |
| 3,505,785 | 4/1970 | Kirkland | 55/67 |
| 3,622,367 | 11/1971 | Hang et al. | 252/62.52 |
| 3,700,499 | 10/1972 | Haack et al. | 252/62.54 |
| 3,853,987 | 12/1974 | Dreyer | 424/1 |
| 3,977,984 | 2/1976 | Roberts | 252/62.54 |
| 4,001,288 | 1/1977 | Gable et al. | 252/62.52 |

OTHER PUBLICATIONS

Hersh et al., Clinica Chimica Acta, 63 (1975), 69–72.
Nye et al., Clinica Chimica Acta, 69 (1976), 387–396.

*Primary Examiner*—Benjamin R. Padgett
*Assistant Examiner*—Christine M. Nucker
*Attorney, Agent, or Firm*—Cushman, Darby & Cushman

[57] ABSTRACT

This invention relates to magnetic particles and to the use thereof. Each particle comprises a low density core and a component therewith, at least a portion of the surface of the core being coated with magnetic material.

25 Claims, No Drawings

MAGNETIC PARTICLES FOR IMMUNOASSAY

This invention relates to magnetic particles and to the use thereof.

Magnetic particles have previously been used, for example, for supporting organic molecules. They have the advantage over earlier systems using particles in that they can be transported or stationed by a magnetic field and they can be retrieved, even from liquors containing colloids or undissolved colloids, by the use of a suitable magnetic device. However, the magnetic particles used hitherto have had a high density, e.g. of the order of 5 gm/cc; thus they tended to settle under gravity unless vigorously stirred, and they also tended to crush large organic molecules.

We have now found that the disadvantages mentioned above may be overcome by the use of composite magnetic particles comprising a low density core and having a magnetic coating over at least a proportion of their surface. The density of such particles can be chosen to suit a range of applications.

The present invention provides composite magnetic particles, each particle comprising a low density core and a component associated therewith, at least a proportion of the surface of the core being coated with a coating of magnetic material. Preferably the composite magnetic particles are in the form of spheres.

By "low density" we mean that the average density of the particles is less than 3.5 g/cc, preferably less than 2.5 g/cc, and particularly preferably less than 1.5 g/cc.

Within the term "associated" we include mechanical entrapment of the component in the core or vice versa and physical and chemical attachment of the component to the core and/or to the coating of magnetic material.

Where mechanical entrapment of the associated component occurs, the core may be formed by cross-linking a material such as polyacrylamide, silica gel, or starch in the presence of the associated component. Alternatively, the associated component may be cross-linked to encapsulate the core. Preferably however the associated component is attached to the core and/or the magnetic coating, e.g. the associated component may be in physical contact with a surface active material such as alumina, carbon, clay, ion-exchange resins, cellulose or glass. More preferably the associated component is chemically bound to the core and/or the magnetic coating via covalent bonds.

The nature of the associated component may range from low molecular weight compounds such as amino acids, vinyl monomers or hydrocarbons to high molecular weight natural or synthetic polymers. While the associated component may have no functional groups, i.e. it is a hydrocarbon, preferably it has at least one functional group, particularly preferably it is biologically active, e.g. a drug, hormone or enzyme and more particularly preferably it is a protein.

Composite magnetic particles according to the invention may be moved or stationed by magnetic means such that the associated component may be employed as required. For example, where the associated component is a drug, the composite magnetic particles may be moved through a living organism and located at a point where the drug is required to operate. For example, where the associated component is an amino acid, the amino acid may be employed at one step in the synthesis of a protein and recovery of the product of this step may be facilitated. For example, where the associated component is an enzyme e.g. a proteolase, amylolase, dehydrogenase, oxidase, hydroxylase or glycolase, typical enzymatic reactions may be effected, e.g. conversion of aldosugars to ketosugars and the resolution of amino acids, and such enzymatic reactions are often more efficient than with conventionally immobilised enzymes.

Where the associated component has a biological affinity for a substance the composite particles may be used in so-called affinity chromatography.

Accordingly a further embodiment of the invention provides an affinity chromatographic process comprising the steps of bringing a liquid medium containing a substance into contact with a plurality of composite magnetic particles, recovering the composite magnetic particles by magnetic means and removing the substance from the recovered composite magnetic particles wherein each particle comprises a low density core and an associated component, at least a proportion of the surface of the core being coated with a coating of magnetic material and the substance and the associated component having a specific biological affinity for each other.

By the term "biological affinity" we mean the natural affinity demonstrated by biological systems in biological interactions such as antigen-antibody, enzyme-inhibitor, and hormone-carrier interactions.

Removal of the substance from the recoverd composite magnetic particles may be effected by treating them with a displacing agent or by changing the pH or ionic strength of a liquid with which they are in contact.

By this technique it is possible to isolate proteins, polysaccharides, glycoproteins, steroids, nucleic acids, other classes of naturally occurring compounds, bacteria, viruses and whole cells. Where the reactions on which the biological affinity is based are reversible it is often possible to use this technique to isolate either of the reactants.

Thus where the associated component is an antigen the composite magnetic particle may be added to a solution containing the antibody specific to the antigen, the antibody-antigen complex is formed on the composite magnetic particles which are then recovered by magnetic means e.g. a magnet. The antibody may then be removed from the antibody-antigen complex, e.g. by changing the pH of a medium with which the recovered composite particles are in contact so that one is able to isolate and purify antibody which does not contain residual antigen. Preferably the antigen is a protein although we do not exclude the possibility that it may be a smaller molecule e.g. a steriod or sugar.

Where the associated component is an antibody it is possible to recover whole cells, which have a specific affinity for the antibody.

Examples of antigens against which antibodies can be obtained include inter alia, plasma proteins, enzymes and many hormones. Examples of such hormones are steroids, insulin, gonadotropins, growth hormone, ACTH, thyrotropin and parathromone.

Antibodies can be prepared by any method known per se, by immunising animals by, for instance, repeated subcutaneous injections of small amounts of the appropriate antigen, possibly combined with a so-called adjuvant, such as Freund's mineral oil emulsion, into an animal. The antibodies produced in the animal can be recovered from the blood serum of the same. The protein fraction, which contains the antibody, can be separated by conventional methods, e.g. by precipitating the serum with suitable amounts of a saturated aqueous solution of ammonium sulphate, and then subjected to affinity chromatography.

A further embodiment of the invention provides a method of immuno-assay comprising the steps of reacting an antigen with an antibody one of which is the associated component of a composite magnetic particle, separating the composite magnetic particle from the reaction mixture and assaying the recovered particles or reaction mixture, the composite magnetic particle comprising a low density core and an associated component, at least a proportion of the surface of the core being coated with a coating of magnetic material.

Assay is preferably effected by radioisotope techniques, i.e. so-called "radioimmuno-assay" where a labelled antigen is employed and so-called "immunoradiometry" where a labelled antibody is employed, although we do not exclude the possibility that fluorescent, enzymatic viral or nephelometric techniques may be employed.

Radioisotope techniques are based on the ability of an antibody to bind its antigen irrespective of whether they are labelled with a radioactive isotope or not, binding of labelled and unlabelled material taking place in proportion to the concentration of labelled and unlabelled material respectively. Such techniques may be employed to assay antibodies or antigens which are capable of being purified and labelled with a radioactive isotope.

Where a radioisotope technique is employed for assay, a known quantity of an isotopically labelled antigen or antibody in solution is added to a solution of the unlabelled antigen or antibody which it is desired to assay, a known amount of the corresponding antibody or antigen as the associated component of composite magnetic particles is added to the mixture of labelled and unlabelled antigen or antibody, and incubated. The composite magnetic particles are separated from the solution by magnetic means, e.g. they may be drawn to the bottom of the solution, and preferably a sample of the remaining solution techniques. From comparison with a standard curve obtained by performing the process hereinbefore described with a range of concentrations of labelled antigen or antibody, the amount of unlabelled antigen or antibody in the solution which it is desired to assay may be determined. However we do not exclude the possibility that the composite magnetic particles may be "counted" to effect the determination.

Since the associated component is firmly attached to an insoluble carrier, the labelled material, which reacts with and is bound to the associated component in the determination, can be easily separated from the unbound labelled material by magnetic means. The separation is insensitive within physiological limits to variations in the salt and protein concentrations of the liquid in which reaction between antibody and antigen is effected. The test is easy to perform as known amounts of composite magnetic particles according to the invention can be predispensed in test tubes, for instance, and stored without losing the binding ability. The whole procedure including the separation of the free labelled material from labelled material bound to the associated component of the composite particles, can be made in one and and the same test tube without any further addition of precipitants or the like.

Labelling of the antigen or antibody with a radioactive isotope can be effected in a conventional manner, a suitable isotope for the purpose being selected, e.g., $I^{125}$, $I^{131}$, $C^{14}$ or $H^3$. Choice of a particular isotope is a compromise between many factors. Particularly suitable isotopes are tritium and a radioactive isotope of iodine such as $I^{125}$.

The associated component according to this aspect of the invention is preferably a protein. Thus an antibody may be the associated component of the composite particle and an antigen may be assayed. Where an antigen is a protein it may be the associated component and an antibody may be assayed. Where an antigen is not a protein e.g. a sugar or a steriod, its antibody is preferably assayed by the so-called "double antibody" technique in which a second antibody which has a biological affinity for the first antibody is the associated component.

Within the term "solution" we include dispersions and suspensions as well as solutions.

The cores which may be employed in composite magnetic particles according to the invention may be solid, vesicular or hollow. They may be of inorganic or organic material e.g. ceramic, glass, metallic, wood, charcoal, natural or synthetic polymers. The material will be selected with regard to its use and to the conditions to which it will be exposed. Preferably the cores are compatible with the environment in which the composite magnetic particles are to be employed although we do not exclude the possibility that they may be attacked by the environment. Where such attack does occur it should, however, not be detrimental to the effective functioning of the composite magnetic particles. Suitable polymers from which the cores may be made include polystyrene, polyethylene, polypropylene, polyurethane, acrylonitrile/styrene copolymers, polyacrylamide, cellulose derivatives, polyaminoacids, phenol/formaldehyde, urea/formaldehyde. Suitable inorganic materials include non-siliceous metal oxides e.g. alumina, hydroxy apatite, nickel oxide and siliceous materials, e.g. silica, wollastonite, silica gel or bentonite. Glass is often preferred as the core material since it is dimensionally stable, it can be thoroughly cleaned e.g. by sterilisation, to remove surface contamination and it is compatible with a wide variety of environments. Where glass is employed as the core material it is preferably in the form of hollow spheres since they are readily obtained in a range of densities and sizes.

The size of the cores is typically between $10^{-4}$ and 1 cm, preferably between $10^{-3}$ and $2 \times 10^{-2}$ cm diameter, and particularly preferably between $4 \times 10^{-3}$ and $10^{-2}$ cm diameter. Where solid cores are employed, a density suitable for any particular application may be obtained by use of an appropriate material or combination of materials e.g. wood or plastic. Where vesicular cores are employed e.g. of polyurethane foam, a density appropriate for any particular application may be obtained by choice of a suitable formulation. In the case of hollow cores e.g. of glass, or phenol/formaldehyde a density appropriate for any particular application may be obtained by use of an appropriate wall thickness of the cores. The density will be chosen in the light of the particular application. Thus where the composite magnetic particles are required to float on water, a density of less than 1 gm/cc will be used, where the composite magnetic particles are to be suspended in a medium, e.g. in a reaction system having a density of 1.0 to 1.1, the density of the cores will usually be of the order of 1.1 gm/cc, but the precise density will be selected in the light of the particular application.

The magnetic material with which at least a proportion of the surface of the cores is to be coated may be a metallic element, e.g. iron, cobalt, nickel; an alloy, e.g. Alcomax, Hycomax, Alnico, a rare earth/cobalt alloy; an inorganic compound e.g. magnetic iron oxide or any other appropriate material having ferromagnetic properties. Preferably the coating is not magnetised although we do not exclude the possibility that in some applications it may be magnetised. Choice of magnetic coating for any particular application will be made in the light of the nature of the core, the environment in which the composite magnetic particle is to operate and the ease of obtaining the magnetically coated cores. Nickel is often the preferred magnetic coating.

Coating may be effected by any of a range of techniques. A pre-shaped coating may be bonded to the core, a sheet or film of magnetic material may be deformed around the core to adopt the shape of the core or magnetic particles may be pressed into or located on the surface of the core, for example, by adhesion. Preferably the magnetic coating is applied to the core by vacuum deposition, or electrolytic deposition. Electroless deposition is particularly preferred.

Techniques for electroless deposition will be available to the skilled man and may be adapted as appropriate to the desired process. For example, inorganic cores, e.g. glass, may contain active sites to nucleate the electroless deposition although preferably the cores are activated by techniques well known in the art; organic cores, e.g. polymeric, often need to be activated to provide nucleation sites.

Where glass cores are subjected to electroless deposition they are preferably activated prior to the deposition by treatment with a noble metal salt, particularly preferably by treatment with an aqueous solution of palladium chloride, and more particularly preferably the concentration of the aqueous palladium chloride solution is between 0.1 and 0.5% w/w. With lower concentrations of palladium chloride, deposition tends to occur too slowly, and with higher concentrations, irregular surfaces tend to form.

Where cores comprising a polymeric material are subjected to electroless deposition, preferably they are cleaned and their wettability improved prior to the treatment with a noble metal salt. More preferably they are subjected to a low pressure discharge, e.g. a microwave discharge, in an inert gas atmosphere, e.g. argon. The noble metal salt is preferably palladium chloride in aqueous solution. More preferably the polymeric cores, after treatment with the aqueous palladium chloride, are subjected to a low pressure microwave discharge in an inert atmosphere, e.g. in argon, to produce an activated surface suitable for electroless deposition.

Where electroless deposition is employed, the cores are preferably shaken thoroughly with a liquid, typically water, after deposition to remove any loosely bound metal and to improve the smoothness of the surface. Where the cores are inorganic they may be heated for a short time to improve further the surface, e.g. glass cores may be heated to above 250° C., typically to 400° C., for approximately an hour.

The proportion of the surface of the core which is coated with a coating of magnetic material may range from 1% to 100%; preferably more than 50% is coated and it is particularly preferred that more than 80% of the surface of a core is coated. The proportion of the surface of a core left uncoated will depend inter alia on the compatibility of the core and/or coating with the environment, e.g. where the core is attacked by the medium in which the composite magnetic particle is to be employed, it may be necessary to coat substantially the whole of the surface of the core with magnetic material; on the chemical reactivity of the core, e.g. where the associated component may be bound relatively easily to the core it may be desirable to coat only a small proportion of the surface of the core with magnetic material; and on the density of the core and/or coating, e.g. by coating an appropriate proportion of the surface, a composite magnetic particle having a desired density may be prepared. Simple experiment will readily reveal a suitable proportion of coating for any particular application.

The thickness of the coating of the magnetic material will usually be between 2 m$\mu$ and 10$\mu$ although it may be any convenient and appropriate thickness and it need not be constant over the whole of the surface of the core. The thickness chosen will depend inter alia on the method of preparation, e.g. shaped preformed coatings of magnetic material tend to be thicker than coatings deposited directly on the core and on the density of the core, and/or coating, e.g. with a low density core a thick coating may be required to produce a composite magnetic particle of desired density. Simple experiment will readily reveal a suitable thickness of magnetic material for any particular application.

While all the cores employed in any one process are conveniently coated with the same magnetic material to the same thickness over the same proportion of their surface, we do not exclude the possibility that the magnetic material and/or the thickness and/or the proportion of surface coated may be different. By varying these parameters in a mixture of composite magnetic particles fractionation of the composite magnetic particles may be effected.

Where the associated component is covalently bonded to the core and/or the coating of magnetic material by a covalent bond, the covalent bond may be formed directly between the associated component and the core and/or magnetic coating, or by chemical modification of the core and/or associated component e.g. reaction of cyanogen bromide with hydroxyl groups, e.g. of cellulose, to form iminocarbonates. Preferably however coupling agents, e.g. glutaraldehyde, 1-fluoro-2-nitro-azidobenzene, cyanuric chloride or silanes are employed to couple the core and/or the coating of magnetic material to the associated component.

Where the core is a polymeric material the polymer may be selected so that it contains, or can be provided with, suitable reactive groups such as amino groups, hydroxyl groups and carboxylic groups, to readily make possible the binding of associated components to the polymer by bridges with covalent linkages. Alternatively the polymeric core may comprise a three dimensional network held together by covalent linkages. Such cores are often insoluble in a medium in which they are employed although they may be swellable in it. An example of such a polymer is starch which swells in water. However it is often required that the polymeric core particle contains no reactive groups, in which case it will be appreciated that the associated component is attached to the magnetic coating.

Where the cores are inorganic they often have available oxide or hydroxide groups which may be used to form bonds with the associated component; preferably, however, coupling agents are employed to effect bonding between the core and the associated component and more preferably the coupling agents are silanes.

Silane coupling agents are usually molecules which possess two different kinds of reactivity. They are organofunctional and silicon-functional silicon compounds in which the silicon portion of the molecule has an affinity for oxide and hydroxide groups of inorganic materials such as glass, silicates, and metals, while the organic portion of the molecule is tailored to combine with many organic functional groups. In theory, the variety of possible organo-functional silanes useful in this invention is limited only by the number of known organo-functional groups and the available sites on the associated component. A multitude of different silane coupling agents can be used as illustrated by the general formula $(Y'R')_n SiR_{4-n}$ wherein Y' is a member selected from the group consisting of amino, carbonyl, carboxy, isocyano, diazo, isothiocyano, nitroso, epoxy, halocarbonyl; R is a member selected from the group consisting of lower alkoxy, phenoxy, and halo: R' is a member selected from the group consisting of lower alkyl, lower alkylphenyl, and phenyl; and n is an integer having a value of 1–3. Useful silane coupling agents may be represented by the formula: $Y_n SiR_{4-n}$ wherein Y is a member selected from the group consisting of amino, carbonyl, carboxy, hydroxyphenyl, and sulfhydryl; R is a member selected from the group consisting of lower alkoxy, phenoxy, and halo; and n is an integer having a value of 1–3. However, most available coupling agents have the formula $XCH_2CH_2CH_2Si(OR)_3$ wherein R is ethyl or methyl and X is a reactive organic group, tailored to match the reactivity of the system in which it is to be used. X is typically $NH_2-$, $NH_2CH_2CH_2NH-$, $$HS-, \quad CH_2-CH-CH_2O-, \quad CH_2=C-C-O-,$$
$$\phantom{HS-, \quad} \diagdown O \diagup \phantom{CH_2O-,} \quad \phantom{CH_2=}\underset{CH_3}{|}\ \underset{O}{\|}$$

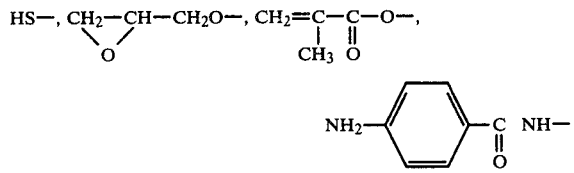

Expoxy silanes such as ω-glycidoxypropyltrimethoxy silane and amino silanes such as N-β-aminoethyl-γ-aminopropyltrimethoxysilane, N-β-aminoethyl-(α-methyl-γ-aminopropyl)-dimethyoxy-methylsilane, γ-aminopropyl-triethoxysilane, γ(p-aminobenzamido)-propyl-triethoxysilane, p-aminobenzenetrimethoxysilane are preferred. These coupling agents may be modified before reaction with the agent e.g. alkyl amino groups may be reacted with carbodiimides or may be converted to isothiocyanoalkylsilane groups by reaction with thiophosgene, and aromatic groups may be converted to diazonium groups by reaction with nitrous acid.

Where silane coupling agents are employed they often form covalent bonds with oxide or hydroxide groups on the magnetic coating.

The coupling agent is conveniently applied to the core having a coating of magnetic material from a solvent solution. Preferably an aromatic or aliphatic solvent is employed, particularly good solvents are toluene, benzene, xylene, and high boiling hydrocarbons. While the silane coupling agents are soluble in polar solvents such as alcohol and water, polar solvents should be avoided because they tend to retard bonding of the silane to the core. Also, aldehydes, ketones, acids, esters, or alkyl chlorides should be avoided as solvents because they tend to react with the silanes.

Bonding of the associated component to the core having a coating of magnetic material is conveniently a two step process: the first step involving bonding of the coupling agent to the core and/or magnetic coating and the second step involving the bonding of the associated component to the coupling agent. The quantity of associated component which may be coupled depends on the amount and nature of the functional groups on the coupling agent and the associated component.

Where the associated component is biologically active the coupling agent is preferably chosen so that the biological activity is not modified or destroyed.

Where the associated component is a protein coupling of the protein to the core having a coating of magnetic material is accomplished by reaction of the coupling agent with the terminal groups and/or pendant functional groups of the protein. Often the proteins to be coupled have sufficient numbers of functional side chains to allow one to select the type of reaction through which attachment could be most easily accomplished. The most frequent site of coupling is through the N-terminal amino group and pendant amino groups contained in lysine residues. The imidazoyl groups of histidine, and the quanidinyl groups in arginine are other amine functions which may be involved in coupling. Covalent coupling may also be effected through the carboxylic acid residues present in glutamic and aspartic acid and through the C-terminal ends of the protein molecule. Another site for coupling is the hydroxyphenyl group present in tyrosyl residues which reacts readily with a diazonium reagent. Finally, coupling can also be effected through formation of a disulphide linkage with the sulphydryl groups present in cysteine residues. Cysteine sulphydryls are also sufficiently nucleophilic to react with glutaraldehyde and other cross-linking reagents.

To reduce the possibility of modifying or destroying the biological activity of a protein it is important that the biologically active sites of the protein are not blocked by the coupling reaction. One of the ways to avoid blocking the active site is to use a coupling technique which does not involve reaction of the functional group present at the biologically active site. The active site can be protected during coupling reactions by employing a covalent blocking reagent, or by performing the reaction in the presence of a substrate or specific inhibitors. Such protection techniques are known. Furthermore the coupling agent should be such that conditions employed or coupling do not destroy the composite magnetic particle or the biological activity of the protein e.g. where pepsin is being attached it must be acid pH since pepsin denatures rapidly above pH5. However we do not exclude the possibility that the biological activity may be modified or destroyed by the coupling action e.g. the pH maxima, Michaelis constant and substrate specificity may be altered thus affording potential for manipulation of enzymes for specific catalytic purposes. A plurality of biologically active associated components may be bonded concurrently or sequentially to the cores and/or the magnetic coating.

The invention is now illustrated by the following Examples in which all parts are expressed as parts by weight unless otherwise stated.

EXAMPLE 1

6.0 gms of hollow glass spheres, diameter approximately 50μ, activated by washing thoroughly with a 0.1% aqueous palladium chloride solution, were added to a coating bath at 55°–60° C. consisting of 112.5 gms of hydrated cobalt sulphate ($CoSO_4 \cdot 7H_2O$), 564.5 gms of sodium potassium tartrate, 330.0 gms of ammonium sulphate, 278.0 gms of boric acid and 132.0 gms of sodium hypophosphite dissolved in 4000 gms of distilled water and adjusted to pH 9.5 with concentrated caustic soda solution. The glass spheres were stirred in the plating solution until coating was judged to be complete by the disappearance of the purple colour of cobalt ions. The spheres were filtered off, shaken with distilled water for 24 hours to remove loosely bound metal from the surface of the spheres, washed with copious amounts of distilled water then acetone and dried in a vacuum oven at 50° C. The spheres were then heated in a muffle furnace for 1 hour at 400° C. to improve the smoothness of the surface.

EXAMPLE 2

The coating process of Example 1 was repeated but using a coating bath consisting of 126.0 gms of nickel ammonium potassium tartrate, 158.5 gms of ammonium sulphate, 238.0 gms of boric acid and 141.0 gms of sodium hypophosphite in 4000 gms of distilled water adjusted to a pH of 9.0 with concentrated caustic soda solution instead of the coating bath of Example 1.

EXAMPLE 3

1 gm of nickel coated hollow glass spheres prepared as in Example 2 was added to 100 mls of a 10 w/v% solution of ω-glycidoxypropyltrimethoxy silane in dry toluene. The mixture was refluxed for 8 hours, the silanised spheres were filtered off, and washed with toluene then acetone.

0.4 gm of the silanised glass spheres were added to 1 ml of a 5% solution of gamma globulin fraction of anti-oestradiol in 0.5 M sodium bicarbonate solution and the mixture kept at room temperature for 48 hours. The particles were then washed with 0.5 M aqueous sodium bicarbonate solution, then with 0.1 M phthalate solution in 1M aqueous sodium chloride at pH 3.0, then in 0.1 M trimethoxyaminoethane in 0.5 M aqueous ethanolamine at pH 7.8.

EXAMPLE 4

The silanisation procedure of Example 3 was followed but using ω-aminopropyl triethoxy silane instead of ω-glycidoxypropyltrimethoxy silane.

1 gm of the silanised glass spheres were refluxed overnight in 100 ml of a 10% solution of thiophosgene in chloroform. The spheres were then filtered off, washed with chloroform and dried in air.

0.4 gm of the glass spheres were then treated with a gamma globulin fraction of anti-β-galoctosidase according to the procedure of Example 3.

EXAMPLE 5

Polypropylene powder of specific gravity 0.93 and average particle size less than 200μ was supported on a polystyrene tray in a "Plasmod" apparatus (ex Nanotech) and subjected to 50 RF for 5 minutes in an argon atmosphere. The powder was then immersed in a 2.5% aqueous palladium chloride solution for 4 minutes, filtered off and dried under vacuum at 40° C. The powder was then placed in the "Plasmod" and subjected to 3 treatments of 5 minutes each as detailed hereinbefore, with agitation between the treatments. The powder was then treated with the coating bath of Example 2 to give nicket coated polypropylene powder. The nickel coated polypropylene powder was then treated with gamma globulin fraction of oestradiol according to the process of Example 3.

EXAMPLE 6

The procedure of Example 5 was repeated but using polypropylene powder of average particle size 600μ instead of polypropylene powder of average particle size 200μ.

EXAMPLE 7

0.2 gm of nickel coated glass spheres with an associated coating of anti-oestradiol prepared as in Example 2 were made up to 20 ml in phosphate buffered saline (PBS) (Solution A). A solution of tritiated oestradiol (2,4,6,7) in PBS was prepared to produce 20,000 disintegrations per μ liter per minute (Solution B). A solution of unlabelled oestradiol in PBS was made up to 1 nanogram/100μ liter (Solution C).

100μ liters of Solution A, 100μ liters of Solution B and 100μ liters of Solution C were mixed and incubated for 24 hours at 4° C. Anti-body-bound oestradiol was then separated from free oestradiol in the magnetic field of a horse-shoe magnet and the supernatent solution was decanted off. 2 ml of scintillation fluid were added to the supernatent solution and the scintillations were counted in a scintillation counter. The count obtained was fed to a computor programme to determine the percentage binding of the labelled oestradiol and the displacement by unlabelled oestradiol. 35% of the labelled oestradiol was found to be bound.

EXAMPLE 8

The procedure of Example 7 was repeated in two further experiments using nickel coated polypropylene powder with an associated coating of anti-oestradiol (a) of particle size less than 200μ prepared in Example 5 and (b) of particle size 600μ prepared as in Example 6 instead of the nickel coated glass spheres. In experiment (a) 50% of the labelled oestradiol was bound to the 200μ particle and in experiment (b) 18% of the labelled oestradiol was bound to the 600μ particles.

What we claim is:

1. Composite magnetic particles each particle comprising a core having a density of less than 1.5 gm/cc, at least a proportion of the surface of the core being coated with a coating of magnetic material and a biologically active component on the surface of the core and/or the said coating.

2. Composite magnetic particles as claimed in claim 1 wherein more than 50% of the surface of the core is coated with the said coating of magnetic material.

3. Composite magnetic particles as claimed in claim 1 wherein the core is a sphere.

4. Composite magnetic particles as claimed in claim 3 wherein the sphere is a thermoplastic material.

5. Composite magnetic particles as claimed in claim 3 wherein the sphere is a hollow glass sphere.

6. Composite magnetic particles as claimed in claim 4 wherein the diameter of the spheres is between $10^{-4}$ cm and 1 cm.

7. Composite magnetic particles as claimed in claim 1 wherein the magnetic material is a metal.

8. Composite magnetic particles as claimed in claim 7 wherein the metal is nickel.

9. Composite magnetic particles as claimed in claim 1 wherein the biologically active component is chemically bound to the surface of the core and/or to the coating of magnetic material.

10. Composite magnetic particles as claimed in claim 9 wherein the biologically active component is bound via a silane coupling agent.

11. Composite magnetic particles as claimed in claim 1 wherein the associated component contains at least one functional group.

12. Composite magnetic particles as claimed in claim 1 wherein the biologically active component is a protein.

13. Composite magnetic particles as claimed in claim 12 wherein the protein is an antibody.

14. Composite magnetic particles as claimed in claim 1 wherein the biologically active component is an antigen.

15. Composite magnetic particles as claimed in claim 1 wherein the biologically active component comprises an antibody-antigen complex.

16. A method of preparing composite magnetic particles as claimed in claim 1 comprising the steps of depositing a metal on the surface of the core, chemically modifying the surface of the core and/or the coating of magnetic material, and then treating the core with the biologically active component.

17. A method of preparing composite magnetic particles as claimed in claim 16 in which a silane coupling agent is reacted with the surface of the core and/or the coating of magnetic material prior to treating the core with the biologically active component.

18. A method of preparing composite magnetic particles as claimed in claim 17 in which reaction with the silane coupling agent is effected in solution.

19. A method of preparing composite magnetic particles as claimed in claim 18 in which the silane coupling agent is reacted with the surface of the core and/or the coating of magnetic material and then with a terminal and/or pendant reactive group of a protein.

20. A method of preparing composite magnetic particles as claimed in claim 19 in which the biologically active group of the protein is blocked before reaction with the silane coupling agent.

21. An affinity chromatographic process comprising the steps of bringing a liquid medium containing a substance into contact with composite magnetic particles as claimed in claim 1, recovering the composite magnetic particles by magnetic means and removing the substance from the recovered composite magnetic particle, the substance and the biologically active component having a specific biological affinity for each other.

22. A method of immunoassay comprising the steps of reacting an antigen with an antibody, one of which is the biologically active component of a composite magnetic particle as claimed in claim 1 separating the composite magnetic particles and the reaction mixture and assaying the recovered composite magnetic particles or reaction mixture.

23. A method of immunoassay as claimed in claim 22 in which assay is effected by a radioisotope technique.

24. A method of immunoassay as claimed in claim 23 in which the radioisotope is $H^3$.

25. Composite magnetic particles as claimed in claim 1 wherein the said coating is not magnetized.